United States Patent [19]
Murray

[11] Patent Number: 5,236,971
[45] Date of Patent: Aug. 17, 1993

[54] DENTAL AND ORTHOPEDIC CEMENT METHOD AND PREFORMS

[76] Inventor: William M. Murray, 145 Bryce Rd., Camp Hill, Pa. 17011

[21] Appl. No.: 904,468

[22] Filed: Jun. 25, 1992

Related U.S. Application Data

[62] Division of Ser. No. 833,323, Feb. 10, 1992.

[51] Int. Cl.$^5$ ................................................ A61K 6/00
[52] U.S. Cl. ........................................ 523/116; 523/113; 523/115; 604/56; 433/201.1; 433/212.1
[58] Field of Search ............... 523/116, 113, 115; 433/201.1, 212.1, 222.1; 604/56

[56] References Cited

U.S. PATENT DOCUMENTS

| | | | |
|---|---|---|---|
| 4,082,722 | 4/1978 | Schmitt et al. | 523/116 |
| 4,376,835 | 3/1983 | Schmitt et al. | 523/116 |
| 4,463,875 | 8/1984 | Tepic | 222/82 |
| 4,527,979 | 7/1985 | McLean et al. | 523/116 |
| 4,551,135 | 11/1985 | Gorman | 604/82 |
| 4,671,263 | 6/1987 | Draenert | 128/92 |
| 4,705,519 | 11/1987 | Hayes et al. | 523/116 |
| 4,808,184 | 2/1989 | Tepic | 604/56 |
| 4,808,228 | 2/1989 | Randklev | 523/116 |
| 4,820,306 | 4/1989 | Gorman et al. | 623/16 |

*Primary Examiner*—Paul R. Michl
*Assistant Examiner*—LaVonda DeWitt
*Attorney, Agent, or Firm*—Thomas Hooker

[57] ABSTRACT

Dental and orthopedic acrylic cements are mixed by forming cement powder into a body in which adjacent particles are bonded to each other while defining a continuous open network of passages extended throughout the body and then brining the body in contact with cement liquid. The liquid is wicked throughout the passages to dissolve the bonds and form a mixed cement without stirring.

29 Claims, 3 Drawing Sheets

DENTAL AND ORTHOPEDIC CEMENT METHOD AND PREFORMS

This is a division, of application Ser. No. 833,323, filed Feb. 10, 1992.

FIELD OF THE INVENTION

The invention relates to cured cements conventionally used as grouting and casting material in dental and orthopedic applications, preforms used in mixing dental and orthopedic cements and related methods.

DESCRIPTION OF THE PRIOR ART

Conventional dental and orthopedic cement is made from a very fine powder including polymethylmethacrylate (PMMA) mixed with methylmethacrylate (MMA) monomer liquid to form a flowable acrylic cement mixture. In most formulations the cement is pourable when first mixed and then becomes doughy. After mixing, the cement is flowed to a prepared application site. Mixed cement is usable for approximately 10 minutes after the start of mixing. The short useful life of the cement places a premium on rapid mixing of the cement and flowing the cement to the application site.

The powder used in making the cement typically includes fine particles of polymethylmethacrylate, polymethylmethacrylate styrene co-polymer, and benzoyl peroxide. Barium sulfate is optionally added to provide X-ray opacity and may constitute approximately 10 percent by weight of the powder. The benzoyl peroxide acts as a chemical initiator and may constitute approximately 2 percent by weight of the cement powder. The cement powder is primarily very small rounded particles of PMMA and PMMA styrene co-polymer. Orthopedic cement powder also includes exceedingly fine particles of PMMA and PMMA styrene co-polymer. Dental cement powder typically does not include the exceedingly fine particles.

The methylmethacrylate (MMA) monomer liquid mixed with the cement powder typically includes dimethyl-p-toluidine and hydroquinone. The dimethyl-p-toluidine is a cold-curing agent which may constitute approximately 2.6 percent by weight of the liquid. The hydroquinone is a stabilizer usually added in very small amounts.

Loose PMMA cement powder is mixed directly with the MMA monomer liquid in a ratio of approximately 40 grams of powder to 20 ml. of liquid. Physical mixing of the powder and liquid is required. The liquid will not flow or wick into the powder uniformly.

One conventional way of mixing the cement is to place the polymer powder in a bowl, add the liquid monomer to the bowl and then stir the powder and monomer to form the cement. In orthopedic applications, the cement is then usually poured into the open barrel of a syringe, a cap is mounted on the syringe and the syringe is actuated to flow cement out the cap and to the application site.

Mixing of the polymer powder and monomer liquid in a bowl tends to entrain air voids in the resultant cement. The voids remain trapped in the cement as the cement is poured into the syringe and are subsequently flowed to the application site. The voids may form pockets in the cured cement which weaken the cement.

To reduce the presence of air voids, PMMA cement is also conventionally mixed within an evacuated closed container having a rotary stirrer attached to a lid. However, such vacuum mixing does not assure that all generated or entrained bubbles are removed from the cement, as a high vacuum cannot be achieved. The homogeneity of the cement mixed by such devices is frequently poor. Centrifugation has also been used to remove voids from mixed cement.

Alternatively, a modified PMMA cement for orthopedic use is mixed from specially formulated polymer powder and monomer liquid within a syringe cartridge having two chambers separated by a frangible wall. Mixing is performed by breaking the wall and compressing the monomer into the powder. The powder and liquid are then mixed. Finally, the cement is extruded from the syringe. Standard PMMA cement cannot be mixed in this way, and the required cartridge is complex and expensive.

SUMMARY OF THE INVENTION

The invention relates to methods for mixing the components of an acrylic cement, typically a PMMA cement of the type presently used for orthopedic and dental applications. According to the method of the invention, acrylic cement powder is preformed into a solid, rigidified body prior to mixing with the liquid monomer. The adjacent particles in the body are held together by relatively weak bonds formed at points of contact while defining a continuous open network of passages extending throughout the body. The rigidified body is sufficiently strong to be handled without breaking.

The cement is mixed by placing the rigidified body and an appropriate volume of liquid monomer together in a container. The liquid quickly wicks into and through the interior passages to a maximum penetration depth. During inward wicking of the liquid the air within the passages is displaced outwardly of the block. The geometry of the block insures that the liquid penetrates a depth into the block sufficient to fill all of the interior passages in the block and completely wet the particles in the block.

The liquid in the block dissolves or breaks the bonds between the adjacent particles so that the block loses its shape and slumps down into the container as the released particles and liquid become pourable. The cement is then ready to be flowed to a desired application site. Alternatively, flowing of the cement to the application site may be delayed until the cement becomes doughy. In either event, with most cement formulations, the cement is preferably mechanically mixed or worked before reaching the application site to improve its mechanical properties. The cement may be flowed to the applications site by extrusion through the nozzle of a syringe. Alternatively, a volume of cement may be poured directly onto the application site.

The use of a preformed rigidified powder block in the mixing step permits very rapid mixing of acrylic cement. It solves the problem of eliminating voids from the mixture. Time is saved over conventional mixing methods and gas voids in the cement are reduced, resulting in stronger cement.

Mixing is easily performed in a syringe without the necessity the mixed cement from a separate mixing container into a syringe. There is no need to mix the cement manually.

The rigidified body and liquid are preferably placed together in a syringe cartridge slightly larger than the body to assure that the liquid contacts the entire surface area of the body for proper wicking into the interior of the body. Large area interior passages may be provided in the body to assure the entire interior volume of the body is wetted. After the body has absorbed all of the liquid and the particle bonds have been dissolved and broken, a cap may be directly placed onto the syringe to permit immediate flowing of the mixed cement to the work site. The cap contains a nozzle with a spiral mechanical mixer to work the cement as it is being flowed from the syringe. Working the cement improves the strength of the cement when set.

The rigidified cement body is preferably made by first forming a compacted body from acrylic cement powder and then rigidifying the compacted body. The compacted body may be made by either of two methods. In the first method, a volume of dry cement powder is compressed in a mold to a desired shape and to a density which permits monomer liquid coming into contact with the surface of the block to wick throughout the interior of the block and fill the internal passages between the particles. The mold may include one or more rods or inserts extending through the mold cavity to define large area interior passages in the molded rigidified block to assure proper wicking throughout the entire volume of the block.

After physical compacting of the powder in the mold, the top and bottom of the mold and any inserts are removed. The powder is compressed sufficiently to form weak cohesion bonds between adjacent particles sufficient to form a stable compacted body held within the sides of the mold.

Alternatively, the compacted body may be formed from bone cement powder by mixing the powder with a small volume of a non-solvent liquid, such as water, to dampen the powder. All of the liquid is retained within the powder mixture. The damp powder mixture is placed in a mold and compressed to bring the particles into intimate contact with each other and form a desired shape. The non-solvent liquid is not absorbed into the cement powder. After compression molding, the liquid is evaporated to form the compacted body. The body may be removed from the mold either before or after drying.

The compacted body may also be made from a mixture of cement powder and non-solvent liquid by a continuous extrusion process. During extrusion, the mixture is compressed to bring the particles into intimate contact. The extrudate has a uniform cross-section and may be severed into portions of a desired length for subsequent evaporation of the liquid.

When dried, the compacted bodies formed from the bone cement powder—non-solvent liquid mixture are held together by cohesive bonds between the adjacent particles in the body, much in the same way as the particles in a dried mudcake are held together.

A compacted bone cement body is formed into a rigidified body by a solvent vapor process. Solvent vapor is flowed through the passages of the compacted powder body. The solvent vapor is adsorbed onto the particles and wets the particle surfaces. At touching points between adjacent particles sufficient solvent is adsorbed to cause solvent bonding between the particles as the solvent is quickly absorbed into the particles. The solvent bonds join adjacent particles to one another and cooperate to form a self-supporting rigidified block with an open network of passages extending through the block. Absorbed solvent is then removed from the particles by evaporation which may be aided by heating and/or by application of a vacuum. The rigidified body is appropriately packaged for subsequent mixing with the monomer liquid.

Other objects and features of the invention will become apparent as the description proceeds, especially when taken in conjunction with the accompanying drawings illustrating the invention, of which there are three sheets and two embodiments.

DESCRIPTION OF THE PREFERRED EMBODIMENTS

Figure 1:
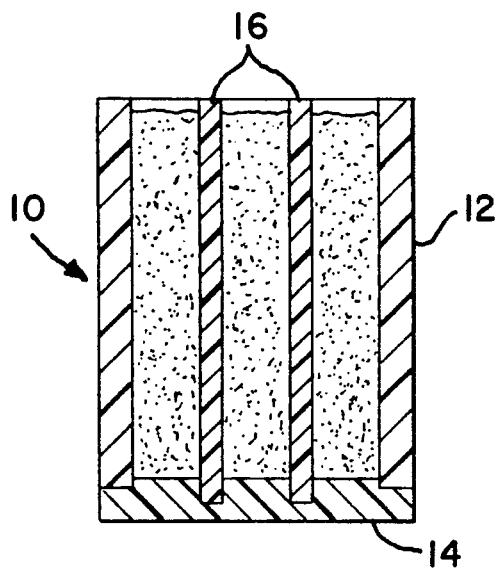
FIG. 1 is a cross section of a mold filled with a loose volume of acrylic cement powder.
Figure 2:
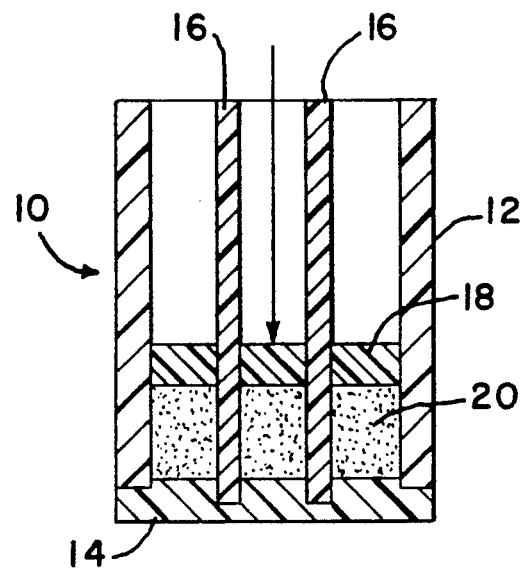
FIG. 2 illustrates the powder after physical compaction.

FIGS. 1 and 2 illustrate a mold for forming loose acrylic cement powder into a compacted body and then a rigidified body. Mold 10 includes a cylindrical side wall 12, a removable bottom wall 14 having six vertically extending insert rods 16 arranged in a circle within the interior of wall 12. A removable top 18 fits within the interior of the wall 12 and is provided with six openings having close sliding fits with the rods 16.

Figure 3:
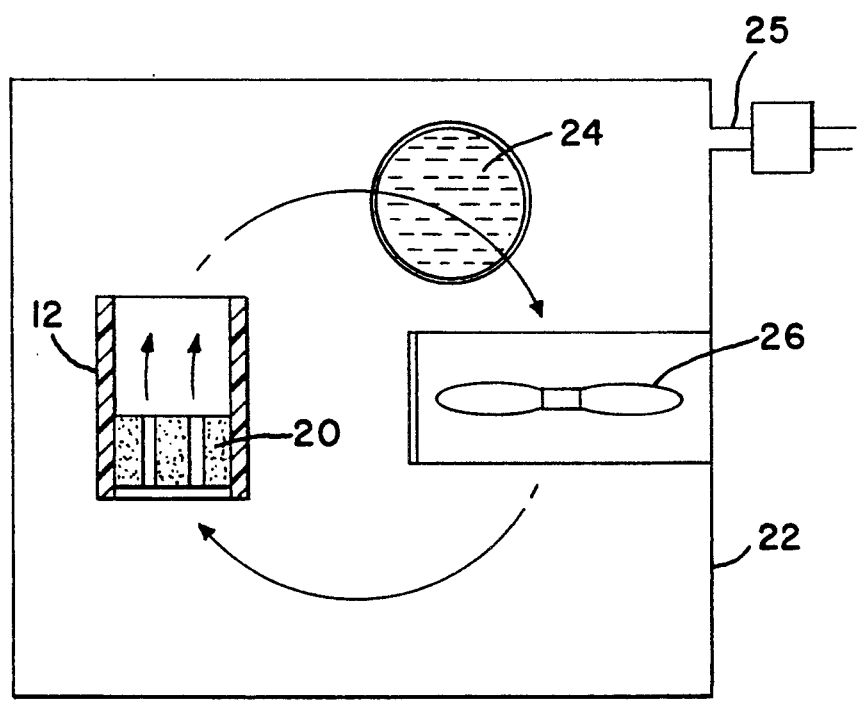
FIG. 3 illustrates treatment of the compacted powder body retained in the sides of the mold to form a rigidified body.

The compacted cement body is formed by using a mold as shown in FIG. 1 with the top removed. The desired weight of loose particulate cement powder is poured into the mold. The powder surrounds rods 16 and fills the mold. The mold may be shaken or vibrated to level the mass of powder and to compact it slightly. Top 18 is then placed on the mold as shown in FIG. 2 and is pressed downwardly into the mold to compact the powder to the desired volume as shown in FIG. 2. The pressure applied to top 18 may be about 200 pounds-per-square inch. The compacting force exerted on the powder is sufficient to form weak cohesive bonds at the junction points between adjacent particles and a resultant compacted body 20. After compacting, the top 18 is removed from the sidewall 12 and the bottom 14 and rods 16 are likewise removed from the sidewall leaving the body 20 within the sidewall as shown in FIG. 3. The volume of the loose bone cement powder placed in mold 10 as shown in FIG. 1 is compressed to a smaller volume as shown in FIG. 2. The correct degree of compaction provides that the interior air passages within body 20 are sufficiently large to assure proper wicking of PMMA monomer liquid throughout the interior volume of the subsequently formed rigidified body. Greater compaction of the bone powder would reduce the volume of the air passages between the particles and hence leave insufficient space for monomer. Insufficient compaction of the powder would deter forming of the cohesive bonds between the particles and would leave large air passages throughout the resultant rigidified body which would not be filled by wicking of the MMA monomer liquid. During forming of a compacted body form loose Simplex brand bone cement powder, the powder was compressed and reduced in volume approximately 60 to 70 percent.

Dental acrylic cement powder, which typically does not include the exceedingly fine ground particles included in orthopedic bone cement powder, needs to be compacted only slightly as it flows more freely and assumes a more compact form than the typical orthopedic bone cement powder. It is difficult to obtain sufficient cohesion of dental acrylic cement powder to form a compacted body by this method.

Alternatively, the compacted body may be made by mixing either orthopedic bone cement powder or dental bone cement powder with a small volume of a non-solvent liquid such as water to form a damp mixture without excess liquid. Sufficient liquid is added to the powder to assure that the mixture holds its shape after compaction by molding or extrusion and evaporation of the liquid. A suitable damp mixture may be formed using two parts by weight of cement powder and one part by weight of the liquid.

The damp mixture may be placed in a mold, compressed to give the desired particle density, and then heated to evaporate the liquid from the mixture. The mixture is not heated to a temperature sufficiently high to injure the cement particles. After evaporation, the particles in the body are cohesively bonded together to form a compacted body similar to body 20.

Alternatively, the damp mixture may be extruded to form an indefinite length extrudate of desired cross-section. The extrudate is severed into bodies having a desired length and then dried to form compacted bodies. During extrusion, the damp mixture is compressed to bring the particles to the desired density.

FIG. 3 illustrates the step of forming a rigidified body from a compacted body. The mold sidewall 12 supporting the compacted body is placed within a closed chamber 22. Alternatively, a compacted body formed from a damp mixture may be placed in the chamber 22 without support by the mold sidewall. A dish of liquid methylmethacrylate (MMA) 24 is also placed in the chamber. The liquid MMA is highly volatile and evaporates to fill the chamber with MMA vapor. Pancake fan 26 circulates this vapor throughout the chamber and through the net-work of interior passages in the compacted powder body.

The solvent vapor is circulated through the passages in the compacted body for enough time to permit sufficient adsorption of MMA monomer onto the surfaces of the particles to form weak solvent bonds between the particles at points of contact. The solvent is then rapidly absorbed into the particles. The body is removed from the chamber before enough MMA monomer vapor is flowed through the passages to dissolve the particles. If desired, atmospheric gases may be removed from closed chamber 22 by vacuum port 25 in order to enhance the diffusion of solvent vapor through the compacted body.

When the body is removed from chamber 22 the absorbed MMA vapor evaporates from the particles and is vented outwardly from the body through the interior passages without destroying the solvent bonds. Evaporation may be accelerated by gentle heating of the body or by the application of a vacuum to withdraw solvent vapor.

Figure 4:
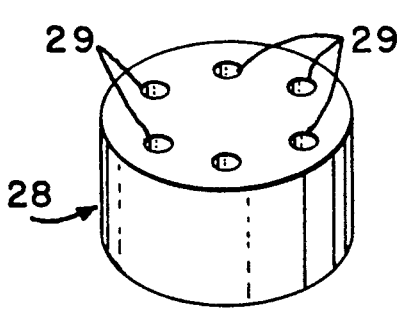
FIGS. 4 and 5 are perspective views of different embodiment rigidified bodies.

The solvent bonds transform the compacted body into a rigidified body 28 as shown in FIG. 4. The rigidified body may be formed from a compacted body formed by one of the previously described methods. As illustrated, rigidified body 28 is cylindrical in shape and includes six large area interior passages 29 formed by rods 16 and extending between the top and the bottom of the body. A body 28 formed from Simplex brand bone cement powder marketed by Howmedica, division of Pfizer Hospital Products of Rutherford, N.J. has a density of approximately 0.74 grams per milliliter.

The method of making rigidified body 28 has been described using MMA monomer liquid vapor as a solvent and flowing this solvent vapor through the compacted body to form solvent bond between adjacent particles. Other solvents may be used.

Figure 5:
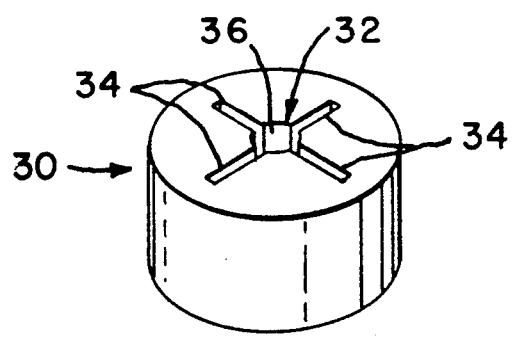

FIG. 5 illustrates a second embodiment rigidified body 30 like body 28 with the exception that body 30 has a single central passage 32 extending the length of the body. The passage 32 includes four 90 degree-spaced radial grooves 34 and a relatively large central opening 36. The central passages 29 in body 28 and central opening 32 in body 30 assure that when the bodies are immersed in monomer liquid, all of the rigidified cement powder in the bodies is located a distance from a surface of the body contacting the monomer liquid less than the maximum wicking or penetration distance of the monomer liquid. This is important in order to assure uniform and equal distribution of the monomer liquid within the body. The monomer will only wick a certain penetration distance into the interior of the body. In experiments using rigidified bodies formed from Simplex brand bone cement powder, MMA liquid has been found to have a penetrating distance of about 10 mm.

Figure 6:
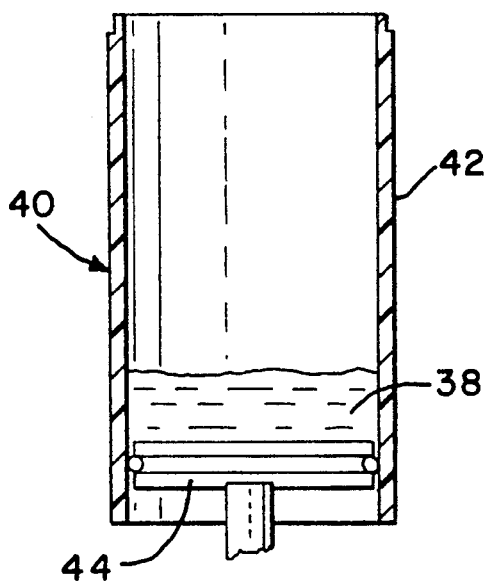
FIGS. 6, 7, 8 and 9 are sectional views taken through a syringe illustrating the steps of mixing acrylic cement using the rigidified body.

FIGS. 6 through illustrate the steps of forming and extruding an acrylic cement using a rigidified body as described. In FIG. 6, an appropriate volume of monomer liquid 38 has been placed in the bottom of an open syringe 40. The syringe includes a cylindrical body 42 and a piston 44.

Figure 7:
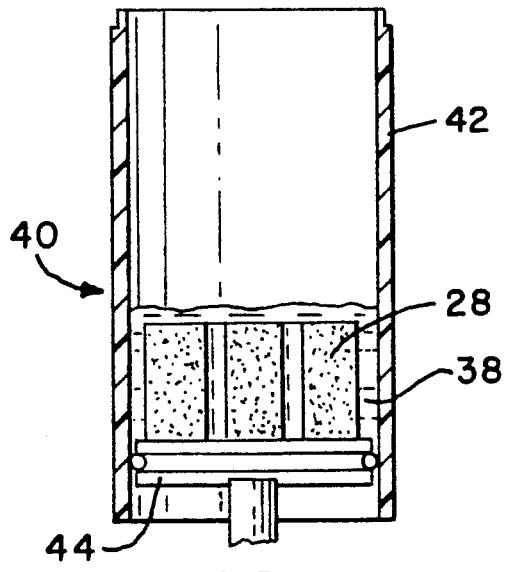
Figure 8:
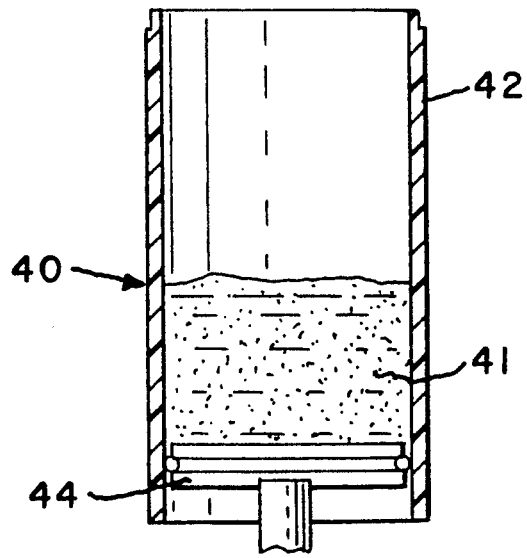
Figure 9:
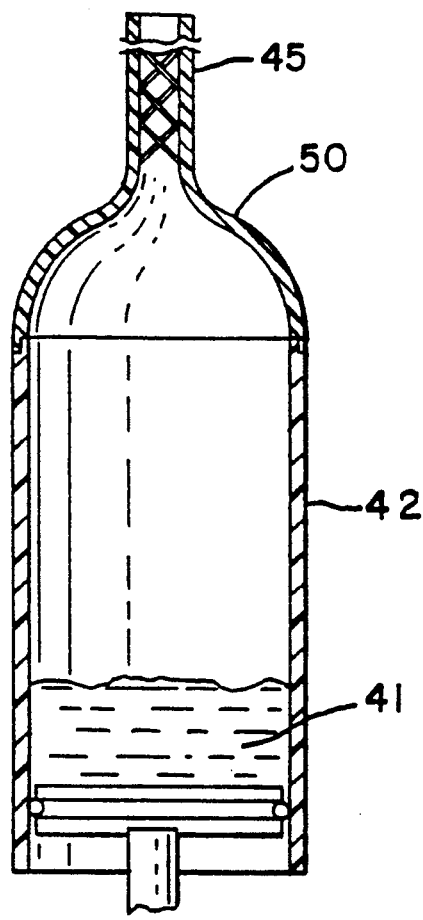

A rigidified body, in this case a body 28, is placed in the open syringe as shown in FIG. 7. The diameter of the body is slightly less than the interior diameter of the barrel 42 to assure that the full exterior surface of the body is exposed to the liquid 38. The body initially displaces the liquid upwardly to a level slightly above the top of body. The liquid fills the interior passages 29 and contacts the top and bottom surfaces of the body Within one to two seconds after the body is placed in the syringe all of the liquid is wicked into and through the interior passages of the body to the maximum penetration depth, thereby assuring that the liquid fills the void spaces within the body. The air previously filling the interior passages is quickly expelled by the liquid.

The liquid absorbed within the body dissolves the solvent bonds between adjacent particles causing the particles to break apart so that the rigidified body collapses and collects in the bottom of the syringe as a mixed cement liquid 41. This dissolution requires slightly more than one minute, with collapse beginning at the bottom of the block an rapidly propagating upward. The liquid cement is comprised of the monomer liquid and the particles making up the former cement powder. The monomer liquid is distributed throughout the liquid in proper proportion for polymerization of the acrylic cement without physical mixing. Significant mixing voids and gas voids are eliminated.

Figure 10:
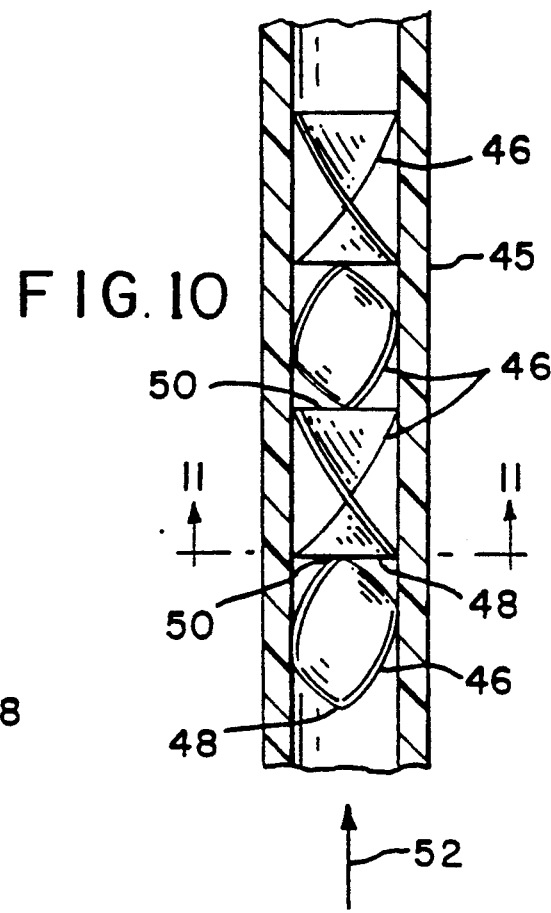
FIG. 10 is an enlarged cross-sectional view of syringe nozzle.
Figure 11:
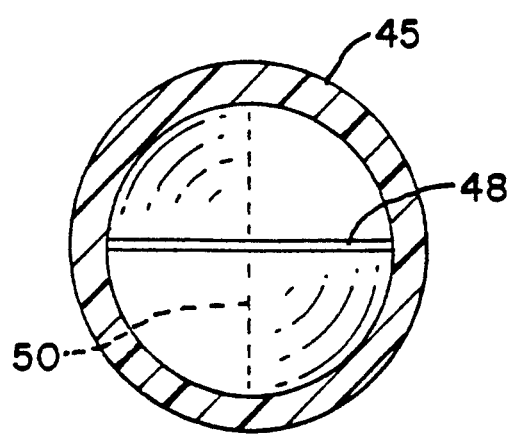
FIG. 11 is a cross-sectional view taken along line 11—11 of FIG. 10.

A cap 50' is then fitted on the syringe barrel 42 to permit extrusion of the cement from the syringe to a prepared application site. The cap includes a nozzle 45 and a series of spiral mixer elements 46 mounted in the nozzle 45 for working the cement during extrusion. Each of the mixer elements 46 fits tightly within the interior of the nozzle 45 and includes a spiral surface dividing the passage in half and having diametrically extending upstream and downstream edges 48 and 50. Liquid cement flowed through the nozzle in the direction of arrow 52 is divided into two equal volume flows by the upstream edge 48 of the mixing element 46 located adjacent barrel 50. These two flows are rotated 180 degrees around the nozzle during flow past each element. The successive elements are oriented circumferentially 90 degrees from each other as shown in FIG. 10 so that the liquid bone cement flowed through the nozzle 45 is successively divided, worked and recombined as it is flowed turbulently past the elements 46. This provides the mechanical working required by most cement formulations for development of maximum strength.

If desired, the mixed cement in the syringe may be extruded while liquid or extrusion may be delayed a sufficient time to allow the consistency of the cement to change from a pourable liquid to a doughy consistency.

While I have illustrated and described a preferred embodiment of my invention relating to making acrylic dental and orthopedic cement and preforms, it is understood that the invention may be used in making dental and orthopedic cements and preforms using non-acrylic powder and liquid. I therefore do not wish to be limited to the precise details set forth regarding acrylic cements, but desire to avail myself of such changes and alterations as fall within the purview of the following claims.

What I claim as my invention is:

1. A preform for use in making dental or orthopedic cement, the preform comprising a body formed from particles of dental or orthopedic cement contacting each other, bonds joining adjacent particles and interior air passages opening on the surface of the body and extending through-out the interior of the body.

2. A preform as in claim 1 including solvent bonds between adjacent particles.

3. A preform as in claim 1 including cohesive bonds between adjacent particles.

4. A preform as in claim 1 wherein said body includes a large area interior passage.

5. A preform as in claim 4 wherein said body is generally cylindrical in shape.

6. A preform as in claim 1 wherein the particles include PMMA particles, the body has a wicking distance for acrylic cement liquid of about 10 millimeters and wherein each particle is located a distance not greater than about 10 millimeters from the surface of the body.

7. A preform as in claim 6 where the density of the body is about 0.74 grams per milliliter.

8. A preform as in claim 7 including solvent bonds joining adjacent particles.

9. A dental or orthopedic cement preform comprising a body of particles bonded to each other, the particles defining an interior network of air passages extending throughout the body.

10. A preform as in claim 9 wherein the passages are dimensioned to permit inward wicking of a cement liquid a distance from the surface of the body and wherein each particle is located within said distance from a surface of the body.

11. A preform as in claim 10 wherein the body is formed from compacted loose cement powder.

12. A preform as in claim 10 wherein said body has a density of approximately 0.75 grams per milliliter.

13. A preform as in claim 12 wherein said wicking distance is approximately 10 mm.

14. A preform as in claim 13 wherein said body includes particles of PMMA.

15. A preform as in claim 9 including solvent bonds joining adjacent particles.

16. A preform as in claim 9 including cohesive bonds joining adjacent particles.

17. A preform for use in making a bone or dental cement, the preform comprising a rigidified body formed from fine particles of polymeric cement, solvent bonds formed form the polymeric cement in the particles joining adjacent particles to each other, and an open network of passages within the interior of the body, the passages extending from exterior surface of the body to the solvent bonds.

18. A preform as in claim 17 wherein the polymeric cement is an acrylic cement.

19. A preform as in claim 17 wherein the polymeric cement is PMMA.

20. A preform as in claim 19 having a density of about 0.74 grams per milliliter.

21. A preform as in claim 17 wherein each solvent bond is located a distance of not more than about 10 mm from the exterior surface of the body.

22. A preform as in claim 17 including a central passage formed in the body.

23. A preform as in claim 17 including a groove formed int he surface of the body.

24. A preform as in claim 17 wherein the body is cylindrical in shape and includes flat top and bottom surfaces.

25. A preform as in claim 24 including a central passage emending into the interior of the body.

26. A preform as in claim 24 wherein said passage extends from the top surface of the body t the bottom surface of the body.

27. A bone cement preform comprising a rigidified body formed from fine particles of PMMA, solvent bonds formed from the PMMA in the particles joining the particles together, and an open network of air and liquid flow passages extending from the exterior surface of the body throughout the interior of the body.

28. A preform as in claim 27 wherein each solvent bond is located within about 10 mm of the exterior surface of the body.

29. A preform as in claim 28 having a density of 0.74 grams per milliliter.

* * * * *

UNITED STATES PATENT AND TRADEMARK OFFICE
CERTIFICATE OF CORRECTION

PATENT NO. : 5,236,971
DATED : AUGUST 17, 1993
INVENTOR(S) : WILLIAM M. MURRAY

It is certified that error appears in the above-identified patent and that said Letters Patent is hereby corrected as shown below:

In the Abstract:

Line 5, change "brining" to --bringing--.

Column 2, line 52, change "applications" to --application--.

Column 2, line 62, after "necessity", insert --of transferring--.

Column 6, line 16, change "90" (in italicized numerals) to --90-- (in plain faced numerals); and line 58, change "an" to --and--.

UNITED STATES PATENT AND TRADEMARK OFFICE
CERTIFICATE OF CORRECTION

PATENT NO. : 5,236,971
DATED : August 17, 1993
INVENTOR(S) : William M. Murray

It is certified that error appears in the above-indentified patent and that said Letters Patent is hereby corrected as shown below:

Column 7, claim 9, line 1, delete "dental or orthopedic"; and line 2, after "of" insert --dental or orthopedic cement --.

Column 8, claim 17, line 4, change "form" to --from--.

Column 8, claim 23, line 2, change "int he" to -- in the --.

Column 8, claim 25, line 2, change "emending" to --extending --.

Signed and Sealed this

Twelfth Day of April, 1994

Attest:

BRUCE LEHMAN

Attesting Officer

Commissioner of Patents and Trademarks